United States Patent [19]

Ross, Jr.

[11] Patent Number: 4,631,393

[45] Date of Patent: Dec. 23, 1986

[54] CALORIE COUNTING DEVICE

[76] Inventor: John R. Ross, Jr., 13020 Long Boat Way, Del Mar, Calif. 92014

[21] Appl. No.: 781,017

[22] Filed: Oct. 30, 1985

[51] Int. Cl.$^4$ .............................................. G06C 3/00
[52] U.S. Cl. .................................... 235/89 A; 235/90; 235/1 R
[58] Field of Search .................... 235/65, 87 A, 89 A, 235/123, 124, 127, 1 R

[56] References Cited

U.S. PATENT DOCUMENTS 1,148,100  7/1915  Krebs et al. ....................... 235/89 A Primary Examiner—Benjamin R. Fuller

[57] ABSTRACT

A calorie counting device comprising a plurality of activity pieces and consumption pieces, a support structure, a balance board and a scale means. The balance board is balanced on said structure along a line that defines a center line. The board has a plurality of locations on one side of said center line for easy placement and removal of activity pieces and a plurality of locations on the other side for easy placement and removal of consumption pieces. Activity pieces represent calories expended during activities. Consumption pieces represent calories consumed. A scale means indicates approximately the net calories gained or lost during a time period or the weight gained or lost during such period.

8 Claims, 4 Drawing Figures

CALORIE COUNTING DEVICE

My invention relates to weight control equipment and more particularly to devices for comparing the number of calories a person expends to the number of calories he or she consumes.

BACKGROUND OF THE INVENTION

Many people are unable to lose weight even when they are dieting and/or excercising for that purpose. The simple answer to weight reduction is that calories expended must exceed calories consumed. But how is a person to know how much he or she is to exercise and how few calories he or she is to consume in order to lose weight at a desired rate? Some charts are available by which calories consumed can be compared with calories expended. Computer programs are also available to help show this comparision. Working with these aids can be complicated and boring. Computers are expensive.

What is needed is a simple, inexpensive device with which a person with a weight problem can easily record on a daily basis the calories consumed and expended and immediately see the impact of that consumption and expenditure on his or her weight over a period of time. That device should be such that it can be placed on the dining table to remind the operator how he or she is doing in terms of weight gain or loss.

SUMMARY OF THE INVENTION

My invention is a calorie counting device comprising a plurality of activity pieces and consumption pieces, a support structure, a balance board and a scale means. The balance board is balanced on said structure along a line that defines a center line. The board has a plurality of locations on one side of said center line for easy placement and removal of activity pieces and a plurality of locations on the other side for easy placement and removal of consumption pieces. Activity pieces represent calories expended during activities. Consumption pieces represent calories consumed. A scale means indicates approximately the net calories gained or lost during a time period or the weight gained or lost during such period.

DETAILED DESCRIPTION OF THE PREFERRED EMBODIMENT

Figure 1:
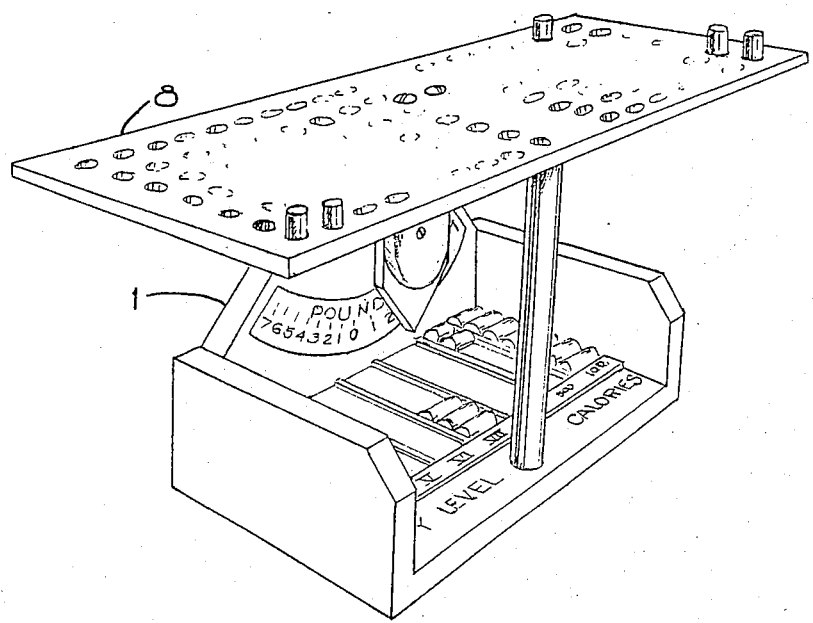
FIG. 1 is a pictorial view of a preferred embodiment of my invention.
Figures 2, 3:
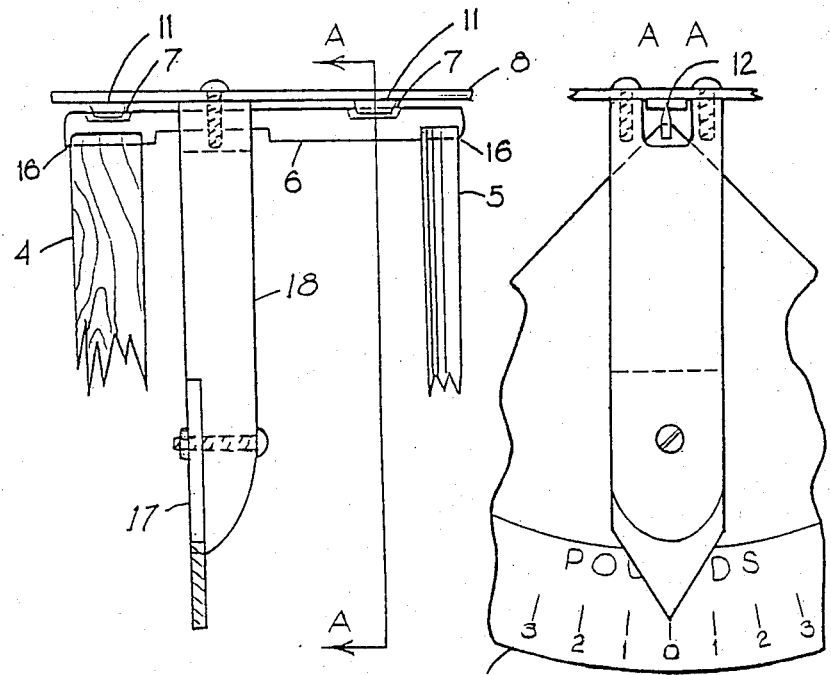
FIG. 2 is a side view of a portion of the above embodiment.
FIG. 3 is a cutaway view of a portion of the above embodiment.

A preferred embodiment of my invention can be described by reference to the figures. The support structure 1 is made of wood. Its functions are to support a balance board 8, provide a rack 2 for holding the activity pieces 22 and the consumption pieces 20 when these pieces are not being used on the balance board and as a mount for the scale 3. Mounted in slots 16 at the top of back support 4 and the front support 5 is a support beam 6 made of brass. At two places on the support beam knife edges 7 have been ground.

A balance board 8 is made of a hardwood board $6'' \times 11'' \times \frac{1}{4}''$. There are 70 holes, 9 drilled equally spaced in each side on a pattern 10 lengthwise and 7 across. A backing of thin cardboard, not shown, has been glued to the bottom of the board on each side so as to form a bottom to each of the 140 holes.

Two $\frac{1}{4}'' \times \frac{1}{4}'' \times \frac{1}{4}''$ pivot blocks 11 are glued to the bottom of the balance board along the center line separating the two sides and passing below the center of gravity of the balance board.

The pivot blocks are made of brass and comprise an inverse "V" 12 cut into the bottom of the pivot blocks along the center line of the balance board. The pivot blocks are located so that the inverse "V" will fit above the two knife edges of the support beam.

Figure 4:
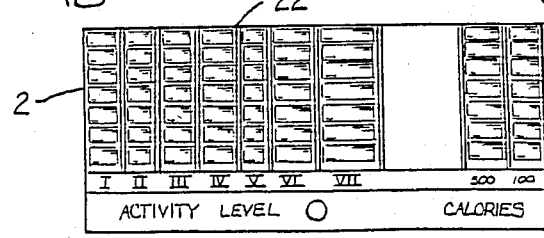
FIG. 4 is a top view of the rack portion of the above embodiment.

FIG. 4 is a top view of the rack 2. On this rack are spaces for seven sets of activity pieces 22. The activity pieces represent seven levels of activity. The pieces in each set have a weight which is approximately proportional to the number of calories consumed by a person engaged in a level of activity represented by that set. (The proportion for a 150 pound person is about 154 calories equals 1 gram.) The pieces are cylinders made by cutting appropriate lengths from 5/16" diameter rods. Levels I and II are wood, III and IV are aluminum, V and VI are brass and VII is copper. The following table gives the appropriate information for the activity pieces for a person who weighs approximately 150 pounds:

| Level | Activity | Rate Range (Nominal) (Cal/Hr.) | Activity Piece Weight (Gm) | Material | Length (Cm) |
|---|---|---|---|---|---|
| I | Sleeping | 40–80 (60) | .40 | W | 1.00 |
| II | Resting Television Driving Car | 80–120 (100) | .65 | W | 1.67 |
| III | Standing Walking Slowly | 120–200 (160) | 1.04 | Al | 1.00 |
| IV | Walking 2–4 MPH Tennis Doubles Swimming 20 yd/min | 200–360 (280) | 1.82 | Al | 1.34 |
| V | Walking 4–5.5 MPH Tennis Singles Swimming 40 yd/min Bicycling 10 MPH | 360–600 (480) | 3.12 | Br | 0.86 |
| VI | Running 6–10 MPH Cross-Country Skiing | 600–1000 (800) | 5.19 | Br | 1.44 |
| VII | Running 10–12 MPH | 1000–1800 | 9.09 | C | 2.06 |

A person who weighs 120 pounds will use about 10% fewer calories than a 150-pound person performing the same activity, and a person weighing 190 pounds will use about 10% more calories. So, in my preferred embodiment, I have three sets of activity pieces so that the embodiment can be used by persons in each of the three weight ranges. The material and lengths of the activity pieces for the 120-pound person and the 190-pound person are set forth below:

| Level | 120 POUND | | | 190 POUND | | |
|---|---|---|---|---|---|---|
| | Cal/Hr | Material | Cm | Cal/Hr | Material | Cm |
| I | 55 | W | 0.91 | 70 | W | 1.17 |
| II | 90 | W | 1.50 | 150 | Al | 0.72 |
| III | 150 | AL | 0.72 | 200 | Al | 0.96 |
| IV | 250 | AL | 1.20 | 350 | Al | 1.67 |
| V | 450 | Br | 0.81 | 600 | Br | 1.08 |
| VI | 700 | Br | 1.26 | 950 | Br | 1.70 |
| VII | 1300 | C | 1.90 | 1500 | C | 2.22 |

In my preferred embodiment, I have two sets of consumption pieces. One set represents 100 calories, and the pieces weigh about 0.65 grams each. They are made of 5/16" diameter wood cylinders 1.67 cm long. Another set represents 500 calories. The pieces are brass cylinders 5/16" diameter and 0.9 cm long and weigh 3.25 grams.

To operate the board, the operator determines the number of calories he or she has consumed during one day using a food-calorie chart. If, for example, 1900 are consumed, this is recorded on the right side of the board by placing a 500 calorie consumption piece in a third hole from the center line (i.e., 500 calories×3=1500 calories) and a 100 calorie consumption piece in a fourth hole from the center line (i.e., 100 calories×4=400 calories). The person then determines the number of hours he or she has spent in each level of activity. For example, if the activities had been 8 hours sleeping, 4 hours resting and driving, 9 hours driving or walking slowly, and 3 hours bicycle riding, the person would place a Level I piece in the eighth hole from the center line on the left side, a Level II piece in the fourth hole, a Level III piece in the 9th hole and a Level IV piece in the third hole. This recording is continued for one week until at the end of the each of the seven columns on the balance board will have been used.

If the calories expended during the week exceed the calories consumed, the board will tilt downward on the activity side. The pointer 14 will point to the weight lost during the week on the weight scale 15. The pointer is comprised of a wooden arm 18 and a brass head 17. The size of the brass head is chosen to provide the appropriate degree of tilt for a given calorie differential. The heavier the head the smaller the tilt for a given differential. Since approximately a 3500 calorie excess or deficiency is equivalent, respectively, to one pound gain or loss, the scale can be calibrated by placing 500 calorie consumption pieces in the seventh holes. Each piece so placed represents 3500 calories (500 calories×7) and approximately one pound gain or loss. Two pieces in the seventh hole represent two pounds. Seven pieces in the seventh holes represent seven pounds.

The foregoing description of the present invention has been presented for the purpose of illustration and is not intended to limit the invention to the precise form disclosed. It is, therefore, to be understood that within the scope of the appended claims, the invention may be practiced otherwise than specifically described.

I claim:

1. A calorie counting device comprising:
   a support structure,
   a plurality of activity pieces comprised of solid matter, each piece representing a level of human activity and having a weight approximately proportional to the number of calories expended by a particular type of person engaged in said level of activity for a particular period of time,
   a plurality of consumption pieces comprised of solid matter, each piece representing a number of calories consumed in food and/or drink and having a weight approximately proportional to said number of calories,
   a balance board balanced on said structure along a line on said balance board defining a center line, said center line defining two sides of said balance board, such balance board comprising a plurality of location means for easy placement and removal of said activity pieces on one side and said consumption pieces on the other side, and
   a scale means disposed on said support structure to indicate the net calories gained or lost during a time period or the net weight gained or lost during such period.

2. The calorie counting device of claim 1 wherein such activity pieces comprise at least three sets of activity pieces, each set representing a different level of activity and the pieces of each set having approximately the same weight, such weight being approximately proportional to the number of calories expended in one hour of the activity represented by the set.

3. The device of claim 2 wherein the scale means comprises a pointer means attached to said balance board and a graduated scale positioned so that as the board tilts the pointer means will indicate the degree of tilt on said graduated scale.

4. The device of claim 3 wherein the scale is graduated in units of pounds, grams, kilograms or calories gained or lost.

5. The device in claim 3 wherein the pointer means comprises a pointer arm with a length at least ½ of the longest dimension of the balance board.

6. The device in claim 5 wherein said pointer means also comprises a tip piece made of a material substantially denser than the rest of the pointer arm.

7. The device in claim 1 wherein said plurality of location means comprises holes in said balance board spaced in rows and columns said rows being approximately parallel to said center line and said columns being approximately perpendicular to said center line.

8. The device in claim 7 wherein the number of holes in each row is at least 7 and the number of holes in each column is at least 10.

* * * * *